United States Patent [19]

Hayashida et al.

[11] 4,443,542
[45] Apr. 17, 1984

[54] PROCESS FOR THE PRODUCTION OF BUTANOL AND NOVEL MICROORGANISM COMPOSITION USED THEREIN

[75] Inventors: Shinsaku Hayashida; Seiya Ogata; Sadazo Yoshino, all of Fukuoka, Japan

[73] Assignee: Idemitsu Kosan Company Limited, Tokyo, Japan

[21] Appl. No.: 354,730

[22] Filed: Mar. 4, 1982

[30] Foreign Application Priority Data

Aug. 20, 1981 [JP] Japan .................................. 56-129452

[51] Int. Cl.$^3$ ................................................ C12P 7/16
[52] U.S. Cl. .................................... 435/160; 435/813; 435/842
[58] Field of Search ................ 435/160, 161, 842, 813

[56] References Cited

FOREIGN PATENT DOCUMENTS 2488272 2/1982 France .................................. 435/160

Primary Examiner—Ferris H. Lander
Attorney, Agent, or Firm—Frishauf, Holtz, Goodman & Woodward

[57] ABSTRACT

A process for producing butanol using a Clostridium microorganism and preferably Clostridium sp. AH-1 (FERM-P 6093, ATCC 39045) in a culture medium containing a cellulose material as the carbon source to produce said butanol and recovering the butanol from the culture medium. The invention also provides a novel composition of said Clostridium sp. AH-1 (FERM-P 6093, ATCC39045).

9 Claims, 2 Drawing Figures

PROCESS FOR THE PRODUCTION OF BUTANOL AND NOVEL MICROORGANISM COMPOSITION USED THEREIN

BACKGROUND OF THE INVENTION

The present invention relates to a process for the production of butanol, and more particularly, to a process for producing butanol utilizing a novel microorganism from cellulose in one step by fermentation.

Acetone-butanol fermentation is known as a process for the production of butanol by fermentation. This fermentation is performed using microorganisms such as *Clostridium butyricum* and *Clostridium acetobutylicum* with starch, molasses, etc. as a carbon source.

Japanese Patent Application Kokai Koho No. 136585/1978 discloses a process for the production of butanol from cellulose as the raw material by fermentation in which the cellulose is first decomposed into sugar liquids and the sugar liquids, e.g. glucose, are fermented to yield butanol. There are no reported processes for the production of butanol directly from cellulose by fermentation.

Cellulose is a major agricultural waste and effective utilization thereof is desired. In the course of extensive study to isolate microorganisms having high cellulose assimilation ability, particularly cellulose-decomposing thermophilic anaerobes having an ability to produce solvents and organic acids, it has been found that a newly isolated strain is capable of assimilating cellulose to produce butanol.

SUMMARY OF THE INVENTION

The present invention provides a process for the production of butanol which comprises cultivating a butanol-producing strain belonging to the genus Clostridium, preferably Clostridium sp. AH-1 (FERM-P 6093, ATCC39045), in a nutrient medium containing a cellulose material as a carbon source to produce butanol and recovering the butanol from the culture medium. The invention also provides (1) novel compositions containing said Clostridium sp. AH-1 (FERM-P 6093, ATCC39045) and also (2) a biologically pure culture of said microorganism strain.

DETAILED DESCRIPTION OF THE INVENTION

The butanol-producing strain for use in the process of the invention is a cellulose-decomposing thermophilic anaerobe belonging to the genus Clostridium. A suitable example is Clostridium sp. AH-1 (FERM-P 6093, ATCC39045), which was isolated from compost.

The characteristics of said strain follow:

| (I) Culture Characteristics | |
|---|---|
| Culture Medium | Growth |
| Bouillon | No growth |
| Bouillon agar | " |
| Gelatin | " |
| Peptone water | " |
| Litmus milk | " |
| Medium having the composition shown in Table 1 | Good growth |

TABLE 1

| | Grams |
|---|---|
| Potassium phosphate monobasic | 1.5 |
| Potassium phosphate dibasic | 2.2 |
| Ammonium sulfate | 1.3 |
| Ferrous sulfate (7 hydrate) | 0.006 |
| Sodium carbonate (10 hydrate) | 4 |
| Yeast extract | 2 |
| Polypeptone | 5 |
| Calcium carbonate | 5 |
| Magnesium chloride (6 hydrate) | 1 |
| Calcium chloride | 0.15 |
| Cysteine hydrochloric acid salt | 0.5 |
| Agar (only in solid media) | 20 |
| Distilled water (containing 5 grams of Avicel or 10 grams of filter paper as the carbon source) | 1,000 ml |
| pH | 7.0 |

Figure 2:
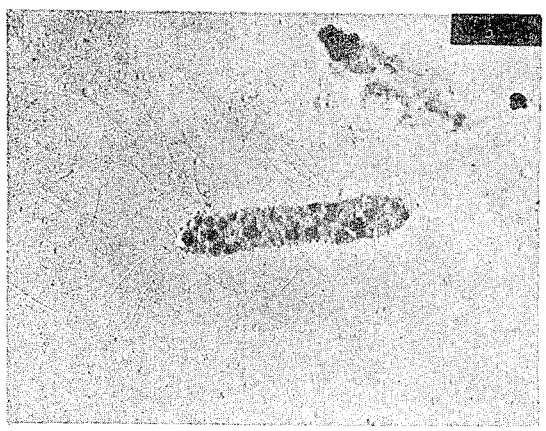
FIG. 2 is an electron microscopic photograph (magnification: ×7000) of the butanol-producing strain for use in the process of the invention.

| (II) Morphological Characteristics |
|---|
| Size: 0.3–0.5μ × 2.0–5.0μ |
| Configuration: rod-shaped |
| Spore: ovoid (0.5–1.0μ × 1.0–1.5μ) |
| Motility: motile, peritrichous flagella (an electron microscopic photograph (magnification × 7000) is shown in FIG. 2) |
| Colony: translucent, white, wavy |

| (III) Physiological Characteristics | |
|---|---|
| (1) Optimum growth conditions | pH 7.0, temperature 60° C. anaerobic |
| (2) Conditions acceptable for growth | pH 6.0–8.0, temperature 45–70° C. |
| (3) Gram's stain | negative |
| (4) Acid-fastness | negative |
| (5) Methyl Red test | positive |
| (6) Voges-Proskauer reaction | negative |
| (7) Formation of indole | positive |
| (8) Formation of hydrogen sulfide | negative |
| (9) Reduction of nitrate | negative |
| (10) Formation of catalase | negative |
| (11) Liquefaction of gelatin and casein | negative |
| (12) Hydrolysis of starch | positive |
| (13) Utilization of citric acid | negative |
| (14) Peptonization of milk | negative |
| (15) Utilization of ammonium salts and glutamic acid | positive |
| (16) Utilization of nitrate | negative |

| (IV) Utilization of Carbon Sources | |
|---|---|
| Carbon Source | Growth* |
| L-Arabinose | + |
| D-Xylose | + |
| D-Glucose | + |
| D-Mannose | + |
| D-Fructose | + |
| D-Galactose | + |
| Maltose | + |
| Sucrose | + |
| Lactose | + |
| Trehalose | + |
| D-Sorbitol | + |
| D-Mannitol | + |
| Inositol | − |
| Glycerin | − |

-continued

| | |
|---|---|
| Starch | + |

In the column of "growth", the symbol "+" indicates "utilizable" and the symbol "−" indicates "not utilizable".

A comparison was made between the present butanol-producing microorganism having the above described microbial characteristics and apparently similar thermophilic anaerobic cellulose-decomposing bacterium with reference to the characteristics of the known strains as disclosed in Bergey's Manual of Determinative Bacteriology, 7th ed. and 8th ed.

The results are shown in Table 2.

TABLE 2

| | Butanol-Producing Microorganism of the Invention | Clostridium thermocellum | Clostridium thermo-cellulaseum |
|---|---|---|---|
| Size (microns) | 0.3–0.5 × 2.0–5.0 | 0.6–0.7 × 2.5–3.5 | 0.35–0.45 × 2.0–4.8 |
| Growth Range Temperature (°C.) | 45–70 | 56–68 | 37–65 |
| pH | 6–8 | | |
| Utilization of Carbon Sources | | | |
| L-Arabinose | + | − | + |
| D-Xylose | + | + | + |
| D-Glucose | + | − | + |
| D-Mannose | + | − | + (weak) |
| D-Fructose | + | − | + |
| D-Galactose | + | − | − |
| Maltose | + | − | + (weak) |
| Sucrose | + | − | − |
| Lactose | + | − | − |
| Trehalose | + | − | − |
| D-Sorbitol | + | − | − |
| D-Mannitol | + | − | − |
| Inositol | − | − | NA* |
| Glycerin | − | − | − |
| Starch | + | − | − |
| Rhamnose | + | NA* | − |
| Ribose | + | NA | NA |
| Sorbose | ± | NA | NA |
| Cellobiose | + | + | + |
| Melibiose | + | − | − |
| Raffinose | + | NA | − |
| Melezitose | − | NA | NA |
| Dextrin | + | − | NA |
| Glycogen | + | NA | NA |
| Inulin | + | − | NA |
| Cellulose | + | + | + |
| Amygdalin | + | NA | NA |
| Esculin | + | NA | NA |
| Salicin | + | − | NA |
| Erithritol | − | NA | NA |
| Dulcitol | + | − | − |
| Adonitol | − | NA | NA |
| Products | | | |
| Ethanol | + | + | + |
| Butanol | + | − | NA |
| Acetic acid | + | + | NA |
| Butylic acid | + | + | NA |
| $H_2$ | + | + | + |
| $CO_2$ | + | + | + |
| $H_2S$ | − | − | NA |

The symbol "NA" indicates "not available", i.e., not disclosed in Bergey's.

In accordance with the process of the invention, the butanol-producing strain is cultivated in a nutrient medium containing a cellulose material as the carbon source.

The term "cellulose material" is used herein to refer to purified cellulose and to cellulosic materials, i.e., plant pulp products such as wood, e.g., pine, cedar, beech, poplar, etc.; stems and bast, e.g., flax, Mitsumata, wheat straw, bagasse, rice hull, etc.; seed hair, e.g., cotton; and to cellulosic materials prepared therefrom such as used paper, e.g., newspapers, magazines, and cardboard; and other fibrous substances substantially derived therefrom. It is desirable to use them after pretreatment such as pulverization, etc., which facilitates the subsequent fermentation of the cellulose to butanol in the process of the present invention.

The amount of the carbon source used in the nutrient medium is usually about 0.5 to 5% (and preferably 1 to 3%) by weight (calculated as cellulose) of the nutrient medium. The specific kind, amount, and so forth of each of the nitrogen source, inorganic salts, and other components necessary for fermentation can be appropriately determined with reference to those usually employed for conventional butanol fermentation, e.g., as disclosed in Nippon Nogeikagaku Kaishi 39, No. 7, p. 247–251 (1965). The nutrient medium may be sterilized by conventional methods.

The fermentation is performed under the conditions wherein the butanol-producing strain produces butanol. Usually, it is performed at a temperature of about 50° to 65° C. and a pH of about 6 to 8 until sufficient butanol is formed and accumulated, usually for 1 to 10 days and preferably for 2 to 7 days.

The thus formed and accumulated butanol is recovered from the nutrient medium by conventional methods. For example, the fermentation broth is separated by centrifugation into solids and liquids (supernatant) which is introduced into a distillation apparatus comprising a stripping column and a concentration and separation column, wherein butanol is distilled and separated.

The butanol-producing process of the present invention produces butanol directly from the cellulose material. Since the butanol-producing strain for use in the process of the present invention is a thermophilic bacterium, the fermentation can be carried out at high temperatures with the advantages that contamination with bacteria is reduced, and that energy can be saved since it is not necessary to control the temperature during fermentation by cooling.

The invention also provides a novel compositions containing the microorganism Clostridium sp. AH-1 (FERM-P 6093, ATCC 39045) and a nutrient medium for cultivating said microorganism.

The following example is given to further illustrate the invention.

EXAMPLE

A medium containing 1% by weight of fine crystalline cellulose (trade name: Avicel) as the carbon source and the other ingredients shown in Table 1 was inoculated with Clostridium sp. AH-1 (FERM-P 6093, ATCC39045), and cultivation was performed at 60° C. for 150 hours.

Figure 1:
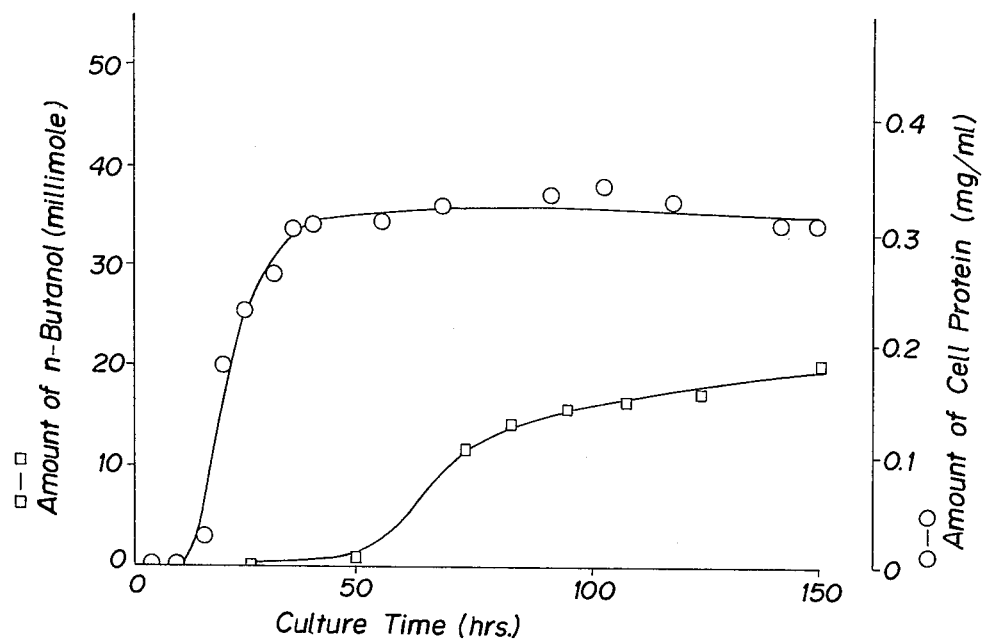
FIG. 1 is a graph depicting the amount of n-butanol produced during a 150 hour culture in accordance with the process of the invention.

The amount of n-butanol formed during the cultivation at various perdiods from the start of the cultivation was measured and plotted. The results are shown in FIG. 1. At the end of 150 hours fermentation, the following products were formed: n-butanol: 1.5 grams per liter; ethanol: 2.1 grams per liter; acetic acid: 1.4 grams per liter; and n-butylic acid: 2.2 grams per liter. FIG. 1 also reports the quantity of cell protein formed over the 150 hour fermentation and therefore the quantity of the microorganim Clostridium sp. AH-1 which was produced during the fermentation.

What is claimed is:

1. A process for producing butanol which comprises cultivating the butanol-producing microorganism Clostridium sp. AH-1 (FERM-P 6093 ATCC 39045), in a nutrient medium containing a cellulose material as the carbon source to assimilate said cellulose directly to produce butanol in a culture medium and recovering the butanol from the culture medium.

2. The process of claim 1, wherein said butanol-producing microorganism has its optimum growth in the temperature range of 50° to 65° C. and carrying out said cultivation at a temperature between about 50° and 65° C.

3. The process of claim 1, wherein said butanol-producing microorganism is a microorganism having a growth temperature range of 50° to 65° C. and the ability to assimilate cellulose, starch and sucrose.

4. The process of claim 3, wherein said cellulose material is a plant pulp product in particulate or fiber form which was prepared by pulverizing said plant pulp product.

5. The process of claim 1 or 2, wherein said cultivation is carried out at a pH of between about 6 and 8.

6. The process of claim 5, wherein said cellulose material is a plant pulp product in particulate or fiber form which was prepared by pulverizing said plant pulp product.

7. The process of claims 1 or 2, wherein said cellulose material is a plant pulp product in particulate or fiber form which was prepared by pulverizing said plant pulp product.

8. A biologically pure culture of Clostridium sp. AH-1 (FERM-P 6093, ATCC39045), said culture being capable of producing butanol from cellulosic materials.

9. A novel compositions consisting essentially of the microorganism Clostridium sp. AH-1 (FERM-P 6093, ATCC 39045) and a nutrient medium for cultivating said microorganism.

* * * * *